United States Patent
Baumgarten et al.

(10) Patent No.: US 8,021,632 B2
(45) Date of Patent: Sep. 20, 2011

(54) REACTOR HAVING TITANIUM SILICATE RECYCLING

(75) Inventors: Goetz Baumgarten, Haltern am See (DE); Martin Roos, Haltern am See (DE); Stephan Schaeflein, Haltern am See (DE); Rolf Augenstein, Marl (DE)

(73) Assignee: Evonik Degussa GmbH, Essen (DE)

( * ) Notice: Subject to any disclaimer, the term of this patent is extended or adjusted under 35 U.S.C. 154(b) by 306 days.

(21) Appl. No.: 12/207,169

(22) Filed: Sep. 9, 2008

(65) Prior Publication Data
US 2010/0063323 A1    Mar. 11, 2010

(30) Foreign Application Priority Data
Sep. 8, 2008  (DE) .................. 10 2008 041 870

(51) Int. Cl.
*B01J 8/00* (2006.01)
*C07C 249/04* (2006.01)
*C07C 249/14* (2006.01)

(52) U.S. Cl. ........ 422/608; 422/606; 422/616; 422/620; 422/225; 422/238; 422/239; 564/253; 564/264

(58) Field of Classification Search .......... 422/606, 422/608, 616, 620, 212, 225, 234, 238, 239; 564/253, 264
See application file for complete search history.

(56) References Cited

U.S. PATENT DOCUMENTS

| | | | |
|---|---|---|---|
| 4,794,198 A * | 12/1988 | Roffia et al. | 564/267 |
| 5,227,525 A * | 7/1993 | Tonti et al. | 564/267 |
| 6,620,970 B2 | 9/2003 | Schiffer et al. | |
| 6,639,108 B2 | 10/2003 | Schiffer et al. | |
| 6,828,449 B2 | 12/2004 | Herwig et al. | |
| 6,828,459 B2 * | 12/2004 | Oikawa et al. | 564/253 |
| 6,861,540 B2 | 3/2005 | Herwig et al. | |
| 6,927,308 B2 | 8/2005 | Leininger et al. | |
| 7,067,699 B2 * | 6/2006 | Oikawa et al. | 564/267 |
| 7,495,129 B2 | 2/2009 | Balduf et al. | |
| 2008/0249300 A1 | 10/2008 | Herwig et al. | |

FOREIGN PATENT DOCUMENTS

| | | |
|---|---|---|
| CN | 200951385 Y | 9/2007 |
| DE | 32 45 318 A1 | 6/1984 |
| EP | 1 468 986 A1 | 10/2004 |
| EP | 1 674 450 A1 | 6/2006 |
| JP | 05068869 A * | 3/1993 |

* cited by examiner

OTHER PUBLICATIONS

U.S. Appl. No. 12/438,295, filed Feb. 20, 2009, Kuppinger, et al. U.S. Appl. No. 12/951,289, filed Nov. 22, 2010, Hengstermann, et al.

*Primary Examiner* — Jennifer A Leung
(74) *Attorney, Agent, or Firm* — Oblon, Spivak, McClelland, Maier & Neustadt, L.L.P.

(57) ABSTRACT

The invention relates to a plant for carrying out chemical reactions, having a reactor (1), the reaction space of which contains hydrogen peroxide ($H_2O_2$) and titanium silicalite (TS-1). The object of the invention is to improve such a plant such that continuous separation and recycling of the active catalyst to the reaction space is possible with a long filter service life. This is achieved in that the reaction space contains a solid silicon source, in that the plant comprises a water takeoff line (3) which is set up for drawing off water in addition to components which are dissolved and/or dispersed therein from the reaction space, in that the water takeoff line (3) leads to a filter (4) which separates off the components which are dissolved and/or dispersed in the water, and in that the plant has a return line (5) which is set up for recirculating to the reaction space components which are separated off by means of the filter (4).

18 Claims, 7 Drawing Sheets

REACTOR HAVING TITANIUM SILICATE RECYCLING

The present invention relates to a plant for carrying out chemical reactions having at least one reactor, the reaction space of which contains hydrogen peroxide and titanium silicalite. Such a plant is known from EP 1 316 545 B1.

In addition, the invention relates to a particular use of this plant and to a process for carrying out a reaction, which process is made possible by the plant.

Numerous chemical reactions carried out industrially take place in the presence of titanium silicalite which serves in these reactions as catalyst. As an example, ammoximation may be mentioned, that is the production of oximes from ketones or aldehydes. With regard to this reaction, reference is made to EP 1 316 545 B1 and likewise to EP 1 191 017 B1, the contents of which are hereby fully incorporated herein by reference.

The said titanium silicalite is a catalyst based on titanium, silicon and oxygen; preferably in a zeolite structure. Such catalysts are obtainable under the product name "TS-1" from Evonik Degussa GmbH.

Under the reaction conditions of ammoximation, the $SiO_2$ fraction contained in the titanium silicalite is soluble in the system. As a result the catalyst becomes depleted in $SiO_2$ due to unsaturated $SiO_2$ streams, such that insoluble, inert, nanoscale $TiO_2$ particles are formed in the reaction space. These very small ceramic particles are discharged from the reactor dispersed in water—which is formed, inter alia, by reaction from $H_2O_2$ and must be taken off from the reaction—and owing to their small size pollute downstream plants for wastewater treatment. Effectively filtering of the catalyst residues is absolutely necessary.

Catalyst solutions are frequently separated using classical separation apparatuses such as, for example, filters, centrifuges or hydrocyclones. In the present case, however, such processes, owing to the nanoscale fraction of active catalyst, do not lead to acceptable catalyst losses in the retentate or in the clear runnings. In addition, there is the discontinuous character of these processes, which can only be incorporated into a continuous reaction procedure with corresponding expenditure.

Figure 1:
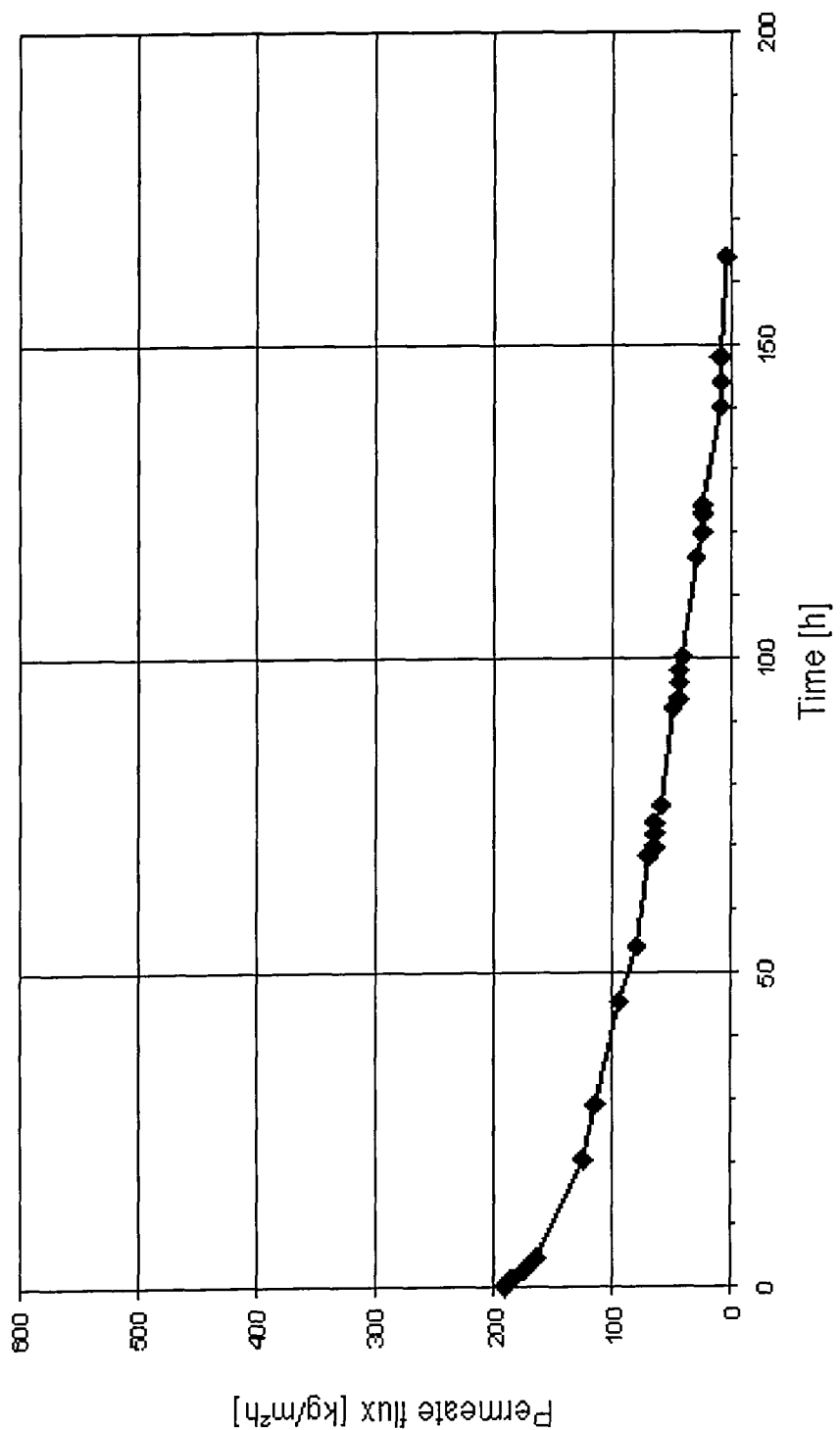

DE 32 45 318 C3 discloses separating off catalyst dispersions using the cross flow filtration process and continuously recirculating them to the reaction. In laboratory experiments, however, it was observed that cross flow filtration using ceramic ultrafiltration membranes cannot readily be combined with ammoximation since the resultant nanoscale $TiO_2$ particles after a short time form covering layers on the ultrafiltration membrane and lead to irreversible blocking of the filter:

FIG. 1 shows the fall in permeate flux of a ceramic membrane having a separation limit of 0.05 μm which is continuously charged under ammoniacal conditions (5% strength $NH_3$ solution) with a 1.5% strength TS-1 catalyst slurry dispersion. Already after 150 hours, the permeate flux had irreversibly fallen to less than 25 kg/m²h. In this case customary operating conditions for the membrane have been selected. The transmembrane pressure was 0.5 bar and the overflow rate about 4 m/s. The permeate yield was below 10%, based on the feed. Scanning electron micrographs show that under the reaction conditions $SiO_2$ is dissolved out of the catalyst and nanoscale $TiO_2$ formed in this case blocks the membrane.

U.S. Pat. No. 7,408,080 B2 proposes preventing the dissolution of titanium silicalite during the ammoximation by adding a liquid silicon source. However, experiments show that this measure, under unfavourable reaction conditions, can lead to an abrupt blockage of the membrane. This is due to the fact that the addition of the liquid silicon source supersaturates the reaction mixture which in turn causes sudden crystallization (precipitation) of the silicon oxides. The precipitated crystal particles abruptly block the filter membrane.

With respect to this prior art, the object of the present invention is to improve a plant of the type mentioned at the outset in such a manner that continuous separation and recirculation of the active catalyst to the reaction space is possible with a long filter service life.

This object is achieved by a plant for carrying out chemical reactions which has at least one reactor, the reaction space of which contains hydrogen peroxide and titanium silicalite, wherein the reaction space contains a solid silicon source, wherein the plant comprises a water takeoff line which is set up for drawing off water in addition to components which are dissolved and/or dispersed therein from the reaction space, wherein the water takeoff line leads to a filter which separates off the components which are dissolved and/or dispersed in the water, and wherein the plant has a return line which is set up for recirculating to the reaction space components which are separated off by means of the filter.

The present invention is based on the finding that, using the addition of a solid silicon sacrificial system, it is possible to stop effectively the dissolution process of the catalyst at the level of the nanoscale catalyst particles, to avoid the formation of inert $TiO_2$, to effectively prevent the formation of irreversible covering layers on filtration membranes and thereby ultimately to increase the filter service life.

Addition of the solid Si sacrificial system enables the reaction to be carried out effectively in the presence of titanium silicalite and hydrogen peroxide on the plant according to the invention in which the catalyst and/or its residues are separated off by means of a filter which is connected to the reaction space by the water takeoff line or by the return line and thus permits recycling of the titanium silicalite which is flushed away with the excess reaction water. The said water is generally not pure $H_2O$, but an aqueous phase of the reaction which contains dissolved, dispersed, or, in particular, suspended, components. The expression "water takeoff line" is therefore generally taken to mean a managed material flow of the aqueous reaction phase in the direction of the filter. This is because it is not absolutely necessary to construct the water takeoff line as a pipe: instead, a plant according to the invention can form within its elements a defined flow profile which comprises a flow path along which the mass stream of the reaction water proceeds. This will be explained in more detail later.

With respect to the use of the solid silicon source, the invention differs from the liquid sacrificial system taught in U.S. Pat. No. 7,408,080 B2. The problem of the sudden precipitation of silicon crystals from supersaturated solution does not occur with the use of the solid, since this always only dissolves in the system to a certain fraction, as permitted by its current solubility. A quasi highly exact self-regulating dosage of the silicon takes place which cannot be achieved with an apparatus structure for dosage of the addition of a liquid silicon source: even if liquid silicon were to be added only dropwise, in the immediate vicinity of the drop in the reaction mixture local supersaturation with silicon would result, which can cause a precipitation reaction. Addition of the solid then significantly lowers the expenditure on dosing apparatus with improvement of the dosage accuracy.

A multiplicity of silicon-containing solids are suitable as Si sacrificial system. Particular preference is given to the use of precipitated silicic acid since this is inexpensive—compared with the catalyst—and therefore can be sacrificed.

The reaction space in which the reaction is carried out need not automatically extend to an individual reactor. It is conceivable to equip the plant with a reactor cascade, that is to say having a multiplicity of individual reactors connected one after the other, each sequential reactor being fed from the overflow of its predecessor. The water takeoff line for the first reactor is then taken to mean a flow path along the overflows through the sequential reactors up to the filter.

When the reaction is a multiphase reaction, taking off the reaction water generally requires a prior separation of the aqueous phase. The phase separation can take place in the reaction space itself, for example by shutting off the agitator, provided that the phases thereupon settle from one another. If this is not the case, or if a continuous process procedure is sought, a liquid/liquid separator can be assigned to the reactor, which separator separates the water which is to be drawn off from the reaction space in addition to components which are dissolved and/or dispersed therein from remaining liquid components which are situated in the reaction space. The reaction and the phase separation then proceed in different elements of the plant. The water takeoff line in this context is taken to mean a flow path from the reactor into the separator and from there to the filter.

The phase separation thus proceeds in the reactor itself, the filter can advantageously be incorporated into the reactor. A pipe for the water takeoff is then in part dispensable, instead, a section would proceed as flow path through the reaction space itself, as a result of which savings in costs are made. The filter can then be constructed, for example, as part of the reactor wall.

A particularly advantageous embodiment of the invention envisages constructing the filter as filter tube which surrounds in the manner of a shell the agitator present in most reactors. The flow through the filter is then maintained by the agitator. Such a situation permits an additional pump to be saved.

Preferably the filter is a membrane filter having a ceramic membrane, since such a separation unit is resistant to aqueous, ammoniacal, $H_2O_2$-containing solution at about 85 to 95° C., as taken off from the reaction space by means of the water takeoff line and passed through the filter during the ammoximation.

Cross flow membrane filters are especially suitable as filters, since they, first, are able to separate off the catalysts reliably, and secondly achieve high continuous filter performance and thus can be integrated into a running industrial process.

Preferably the plant according to the invention is used for carrying out an, in particular, two-phase ammoximation. The advantages achieved according to the invention, however, may also be used in other reactions the system of which customarily dissolves titanium silicalite.

A reaction carried out in the presence of titanium silicalite takes place on the plant according to the invention as follows:
  water having titanium silicalite dissolved and/or dispersed therein is taken off from the reaction,
  the titanium silicalite which is taken off is separated off from the water via the filter and recirculated to the reaction,
  a solid silicon source is added to the reaction.

Preferably, the silicon source is precipitated silicic acid, a solid which is comparatively cheap.

In a particularly preferred embodiment of the invention, the concentration of the silicon source is at least the concentration of the catalyst: the ratio of the mass of the silicon source to the mass of the titanium silicalite is 1:1 in the reaction. The best results are achieved when the ratio is about 3:1, that is three times the concentration of silicon compared with the catalyst.

Taking off the water and returning the catalyst which is separated off can proceed periodically, that is to say after temporary shutting off of the agitator of the reactor, such that spatially separated phases in the reactor form which simplify taking off the aqueous phase. However, a continuous procedure is more economical; this succeeds using a liquid/liquid separator which separates off the aqueous phase of the reaction outside the reactor.

The process according to the invention is outstandingly suitable for carrying out alkaline reactions, especially for carrying out a two-phase ammoximation.

Figure 2:
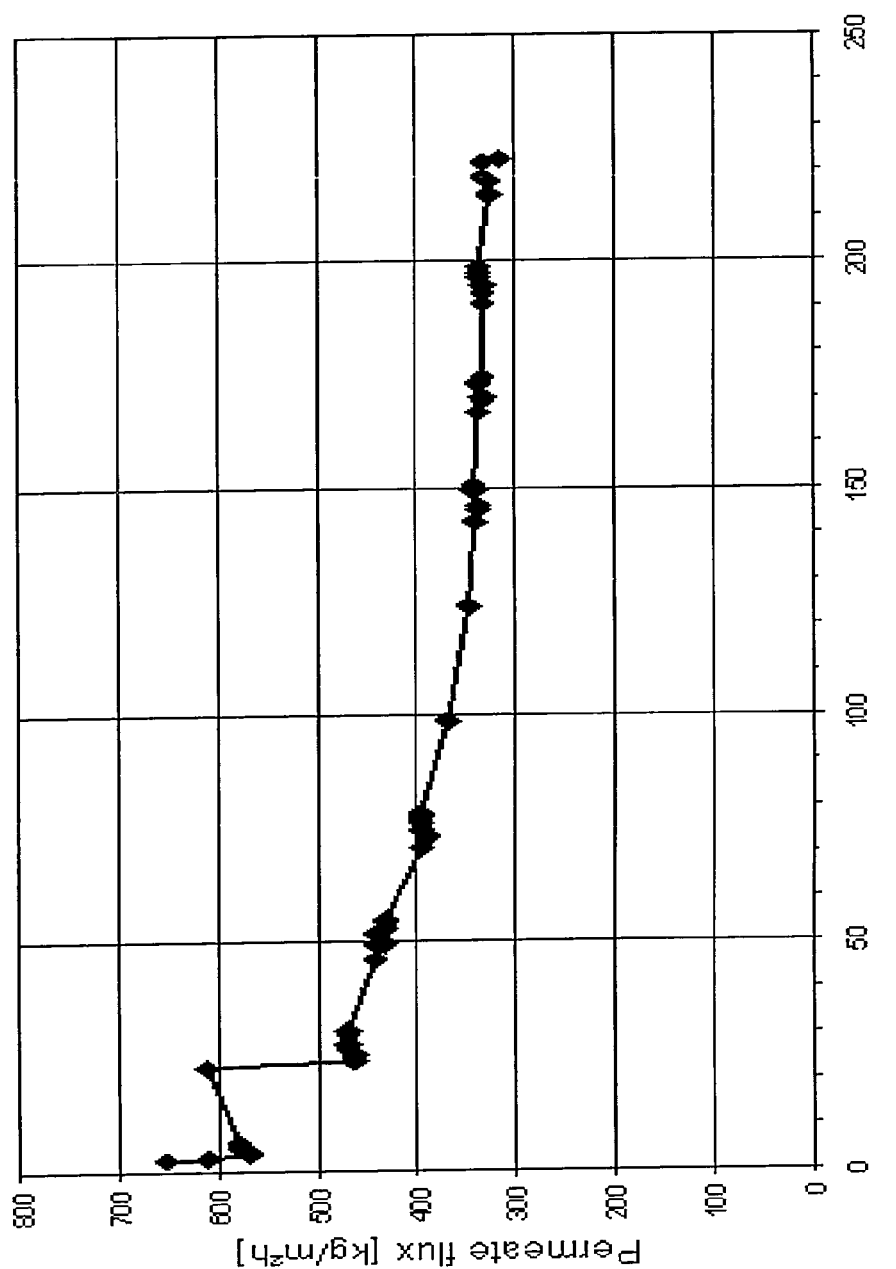
Figure 3:
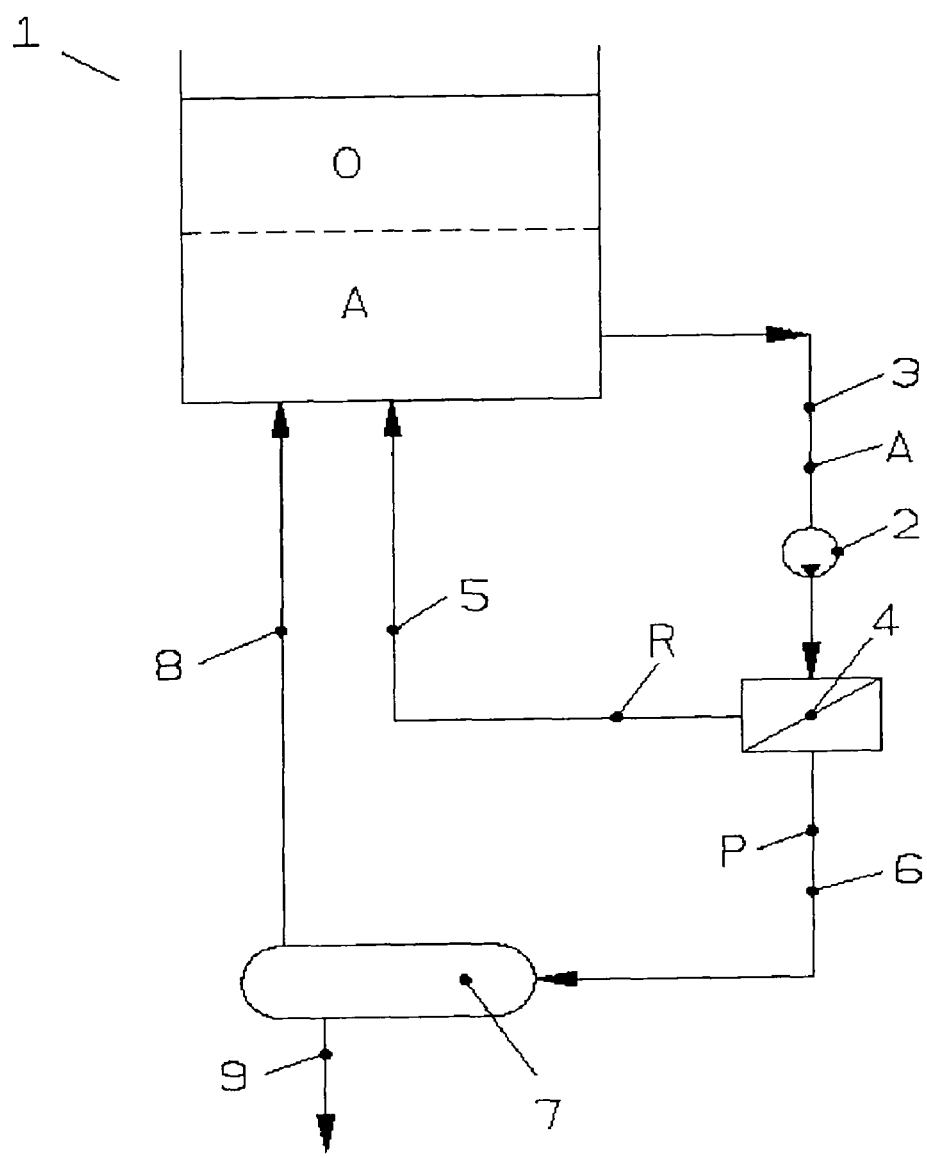
Figure 4:
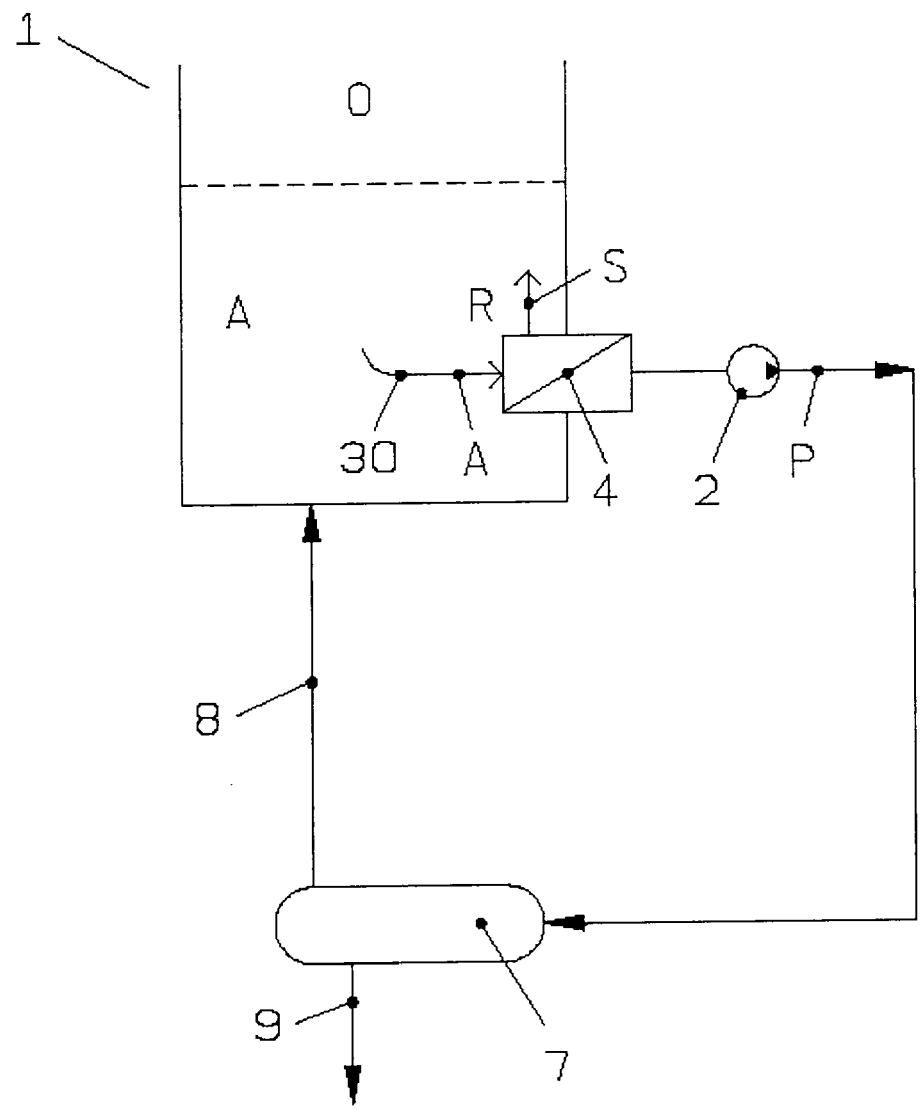
Figure 5:
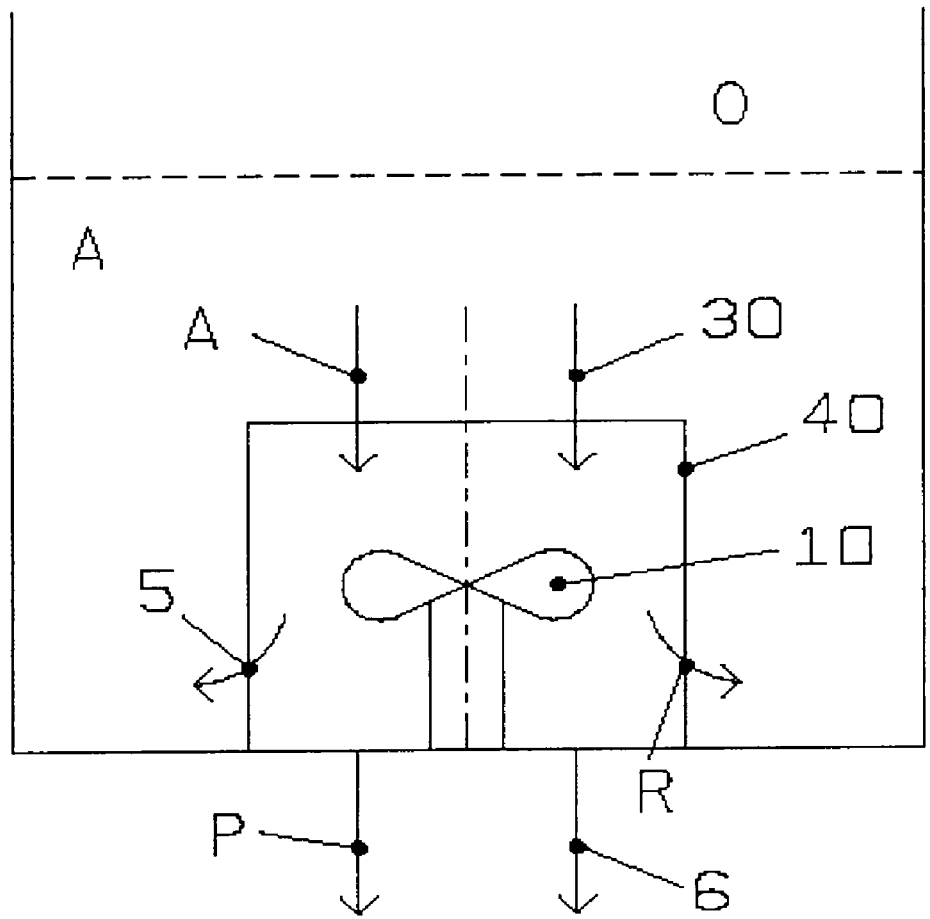
Figure 6:
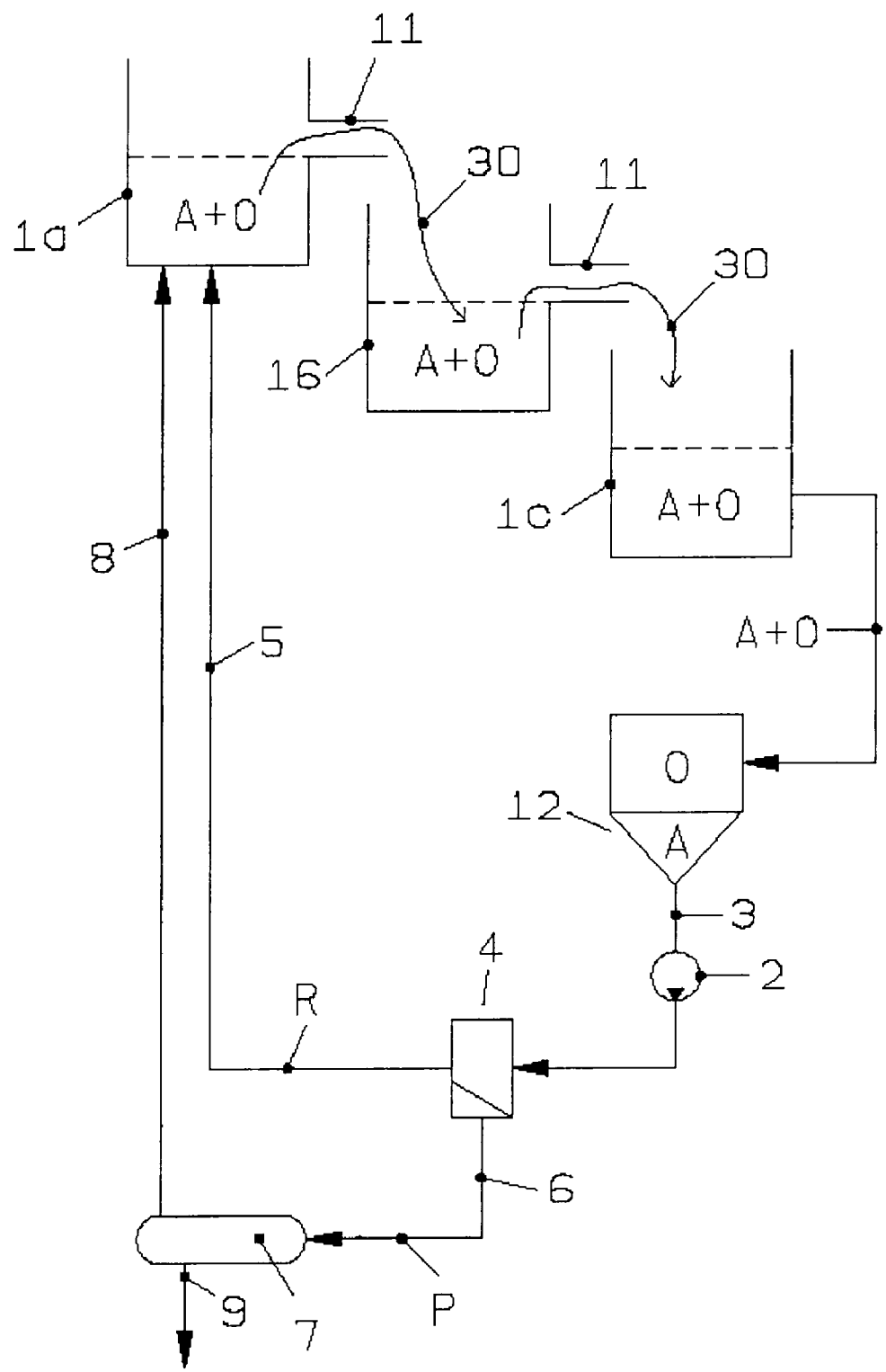
Figure 7:
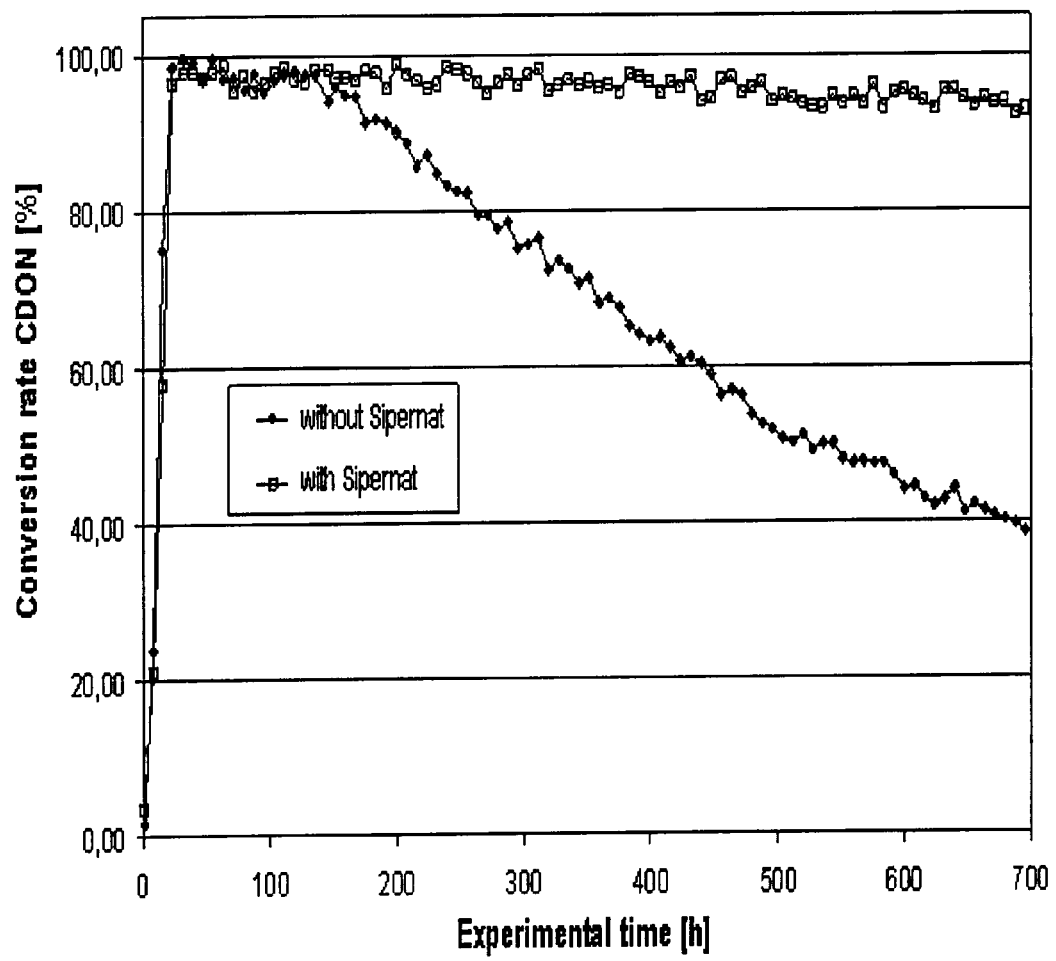

The present invention will now be described in more detail with reference to a preferred exemplary embodiment with the aid of the accompanying drawings. For this, in the drawings:

FIG. 1: shows fall in permeate flux in the separation of TS-1 catalyst slurry using ceramic membrane without addition of silicic acid (prior art);

FIG. 2: shows, as FIG. 1, but with addition of silicic acid (according to the invention);

FIG. 3: shows the connection diagram of a plant having an individual reactor and separate filter (first embodiment);

FIG. 4: shows the connection diagram of a plant having an individual reactor and filter embedded in the wall thereof (second embodiment);

FIG. 5: shows the connection diagram of a plant having an individual reactor and filter tube (third embodiment);

FIG. 6: shows the connection diagram of a plant having a reactor cascade and separate separator (fourth embodiment);

FIG. 7: shows change in the conversion rate of CDON in the plant with and without addition of silicic acid.

The experiment associated with FIG. 1 was described above to explain the problem underlying the invention.

FIG. 2 shows in contrast as an index of the filtration efficiency of the membrane the course of the permeate flux after addition of 1.5% of the solid "Sipernat 320" (a precipitated silicic acid available from Evonik Degussa GmbH) to the 1.5% strength TS-1 (titanium silicalite) dispersion under otherwise identical conditions as in the experiment underlying FIG. 1. It may be seen that the procedure according to the invention brings about an asymptotic approximation to a virtually constant base permeate flux, whereas without addition of Sipernat, the flux through the membrane which is becoming blocked rapidly dries up (cf. FIG. 1).

The reliable separation efficiency of the filter permits construction of a plant for the continuous procedure of a two-phase ammoximation. Nevertheless, periodically driven plants are also subject matter of the invention. A first periodically driven plant is shown symbolically in FIG. 3. It comprises a reactor 1 in which—as taught in EP 1 316 545 B1—a two-phase ammoximation is carried out. In this process, under reaction conditions (pressure: 4 to 6 bar; temperature: 95 to 105° C.) in the reaction space two liquid phases form, an organic phase O and an aqueous phase A. The organic phase O is formed from the starting component cyclodecanone (for short: CDON) and the target component cyclododecanonoxime (for short: oxim) both dissolved in the organic solvent isopropylcyclohexane (called: hydrocumene). The aqueous phase A contains in dissolved form ammonia ($NH_3$), hydrogen peroxide ($H_2O_2$) and also ammonium salts ($NH_4^+x^-$). Suspended in the liquid phase are titanium silicalite (TS-1) and precipitated silicic acid (Sipernat) at three times the concentration. The pH of the aqueous phase is about 9 to 11. Owing to its high content of dispersed fractions, the aqueous phase has the pasty consistency of a slurry, and it is referred to as such. As interphase contactor between W and A, surfactants such as "Marlon PS 30" from Sasol Germany GmbH can be provided. The two phases O and A are, in normal reaction operations, not—as shown in FIG. 3—spatially separated from one another, but are mixed together using an agitator which is not shown in FIG. 3.

In order to remove water which is formed from the reaction from the reactor, the agitator is turned off temporarily, such that the phases as described settle on one another. Then, slurry is pumped off from the reactor space using a pump 2 along a water takeoff line 3 and transported to a cross flow membrane filter 4. The temperature of the aqueous phase A in the water takeoff line 3 is about 85° C. to 95° C. upstream of the filter 4. The ceramic filter membrane of the cross flow filter 4 separates off the solids TS-1 flushed out with the water and Sipernat from the aqueous phase. The retentate R containing TS-1 and Sipernat is recycled as concentrated slurry along a return line 5 to the reactor 1. The permeate P containing water, ammonia and ammonium salts passes further via a permeate line 6 to a distillation apparatus 7. This recovers ammonia dissolved in concentrated form in water; the ammonia passes via an ammonia return line 8 back to the reaction. The residual water having the ammonium salts dissolved therein leaves the plant via wastewater line 9. After a completed recovery cycle, the agitator is turned on again and the reaction continued with mixed phases. The change in operating states proceeds periodically. In order to run the process continuously, two reactors would have to be connected in parallel, of which one is always in the reaction mode while the other recycles.

A higher degree of integration is achieved by the plant of which sections are shown in FIG. 4. The filter 4 here is directly embedded into the wall of the reactor 1, which saves piping. A (very short) section of the water takeoff line 3 runs as flow path 30 within the part of the reactor space which the aqueous phase A occupies. An advantage of this arrangement is that with the lack of a pipe section between reaction space and filter, virtually no pressure drop occurs; the reaction pressure (4 to 6 bar) is exerted directly on the membrane of the filter 4, which, in comparison with the embodiment shown in FIG. 3, increases the permeate flux. Return line 5 for retentate R can then be made short.

In the embodiment shown in FIG. 5, compared with the plant shown in FIG. 4, even the pump can be dispensed with: this is achieved by means of the fact that the filter is designed as a cylindrical filter tube 40 surrounding the agitator 10 which is required in any case in the reactor 1. The agitator 10 rotating coaxially to the filter tube 40 generates a flow profile within the reactor space, which flow profile comprises a mass flow along a flow path 30 of the reaction water through the membrane of the filter tube 40. The mass flow of the retentate R passes back directly through the filter tube 40 into the reaction space. The return line 5 therefore corresponds to an unchannelled flow path.

The above described exemplary embodiments show a clean separation between organic phase O and aqueous phase A within the reaction space. This needs to be sought, since the filter 4 is not in principle suitable for phase separation. If the reaction does not take place between spatially separated phases, phase separation is necessary, for instance by periodic switching off of the agitator 10. This discontinuous process procedure is uneconomic in the two-phase ammoximation; continuous operation must be sought, which permits the plant shown in FIG. 6:

The reaction space of this plant is divided over three reactors 1a, 1b, 1c, which are connected one after the other to form a cascade. The secondary and tertiary reactors 1b and 1c are respectively fed from the overflow 11 of the predecessor 1a and 1b, respectively. The reactor temperature increases from reactor to reactor within the cascade 1a, 1b, 1c in order to increase the solubility of the oxime in the hydrocumene.

The phases A and O are not spatially separate from one another within the reactors 1a, 1b, 1c, but are always mixed with one another. In order, nevertheless, to be able to take off water, a liquid/liquid separator 12 is assigned to the last reactor 1c, which separator performs the phase separation outside the reaction space. The separator 12 acts in a flow-calming manner and, in its lower region, possesses a conical section in which the heavier aqueous phase A settles. From the peak of the conical section, the water takeoff line 3 is constructed as a pipe; starting from the phase A distributed spatially in the cascade up to the said peak, the water takeoff line is taken to mean a flow path 30 through the reactors 1a, 1b, 1c, along the overflows 11 thereof as far as the separator 12. Pipe 3 then leads the reaction water A further via the pump 2 to the filter 4, where the retentate R is filtered off via the return line 5 for recycling of the catalyst. Furthermore, the retentate can also be filtered off upstream of the phase separation, a liquid/liquid separator then must be arranged in the return line.

The plant which is just described permits, owing to addition of the precipitated silicic acid, a continuous procedure of a two-phase ammoximation having a virtually constant conversion rate of CDON:

Thus the effect of Sipernat addition on the reaction of CDON with $NH_3$ (25% strength) and $H_2O_2$ (50% strength) in the presence of TS-1 catalyst slurry to form the oxime was studied in a water/hydrocumene system. Reaction of the feed stream of 1.82 kg/h of CDON proceeded at a temperature profile increasing in a stepped manner from 90 to 105° C. in a cascade of three stirred tank reactors each of 10 l reactor capacity, a subsequent phase separation for separating off product in a separate separator and subsequent membrane filtration for separating off the aqueous phase with recirculation of the catalyst slurry to the reactor cascade. In the system, in the example according to the invention, a TS1 catalyst mass of 1 kg was charged in addition to 2 kg of precipitated silicic acid of the Sipernat type.

In the counterexample, the Sipernat was omitted. From the system, together with the ammonia water and the reaction water at a mass flow rate of 2.56 kg/h, in each case 900 ppm of $SiO_2$ were discharged from the system. As a result of this discharge the catalyst without a sacrificial system (counterexample), after 700 h, was dissolved to such an extent that the CDON conversion of originally 98-99% had fallen to 40%. With the addition of an amount of precipitated silicic acid which is greater than the amount of $SiO_2$ discharged from the system (example according to the invention), the catalyst is retained.

FIG. 7 shows the decrease of the conversion rate of CDON without addition of a Si sacrificial system compared with a system according to the invention to which the Si sacrificial system Sipernat had been added.

The invention claimed is:

1. A plant for carrying out a chemical reactions, comprising:
    a water takeoff line;
    a return line; and
    at least one reactor defining a reaction space of which comprises hydrogen peroxide and titanium silicalite, wherein
    a) the reaction space further comprises a solid silicon source, b) the water takeoff line is set up for drawing off water in addition to components which are dissolved and/or dispersed in the water, from the reaction space, c) the water takeoff line leads to a filter which separates off the components which are dissolved and/or dispersed in the water, and d) the return line is set up for recirculating to the reaction space components which are separated off by the filter; wherein the at least one reactor comprises an agitator, and the filter is a filter tube surrounding the agitator.

2. The plant according to claim 1, wherein the solid silicon source is precipitated silicic acid.

3. The plant according to claim 1, wherein the at least one reactor is a multiplicity of reactors connected one after the other to form a cascade.

4. The plant according to claim 1, further comprising a liquid/liquid separator assigned to the at least one reactor, wherein the liquid/liquid separator separates the water which is to be drawn off from the reaction space in addition to the components which are dissolved and/or dispersed in the water, from remaining liquid components which are situated in the reaction space.

5. The plant according to claim 1, wherein the water takeoff line is, at least in sections, a flow path within a flow profile formed in the at least one reactor.

6. The plant according to claim 1, wherein the filter is a membrane filter comprising a ceramic membrane.

7. The plant according to claim 6, wherein the filter is a cross flow filter.

8. A process for carrying out an ammoximation reaction, comprising: reacting a ketone or an aldehyde to obtain an oxime, wherein said ammoximation reaction is carried out in the plant according to claim 1.

9. A process for carrying out a reaction in the presence of titanium silicalite in a plant according to claim 1, the process comprising:

(A) taking off water from the reaction space via the water takeoff line, said water comprising titanium silicalite dissolved and/or dispersed therein from the reaction;

(B) separating off the titanium silicalite from the water with the filter;

(C) recirculating the titanium silicalite that is separated off to the reaction space via the return line; and (D) adding a solid silicon source to the reaction space.

10. The process according to claim 9, wherein the solid silicon source is precipitated silicic acid.

11. The process according to claim 9, wherein a ratio of a mass of the silicon source to a mass of the titanium silicalite is 1:1 or greater.

12. The process according to claim 9, wherein the water is taken off from the reaction space continuously, and the titanium silicalite separated off is recirculated to the reaction space continuously.

13. The process according to claim 9, wherein the reaction is carried out under alkaline conditions.

14. The process according to claim 13, wherein the reaction is an ammoximation reaction.

15. The plant according to claim 2, wherein the at least one reactor is a multiplicity of reactors connected one after the other to form a cascade.

16. The plant according to claim 2, further comprising a liquid/liquid separator assigned to the at least one reactor, wherein the liquid/liquid separator separates the water which is to be drawn off from the reaction space in addition to the components which are dissolved and/or dispersed in the water, from remaining liquid components which are situated in the reaction space.

17. The plant according to claim 3, further comprising a liquid/liquid separator assigned to the at least one reactor, wherein the liquid/liquid separator separates the water which is to be drawn off from the reaction space in addition to the components which are dissolved and/or dispersed in the water, from remaining liquid components which are situated in the reaction space.

18. The plant according to claim 15, further comprising a liquid/liquid separator assigned to the at least one reactor, wherein the liquid/liquid separator separates the water which is to be drawn off from the reaction space in addition to the components which are dissolved and/or dispersed in the water, from remaining liquid components which are situated in the reaction space.

* * * * *